United States Patent [19]

Ehrenfeld

[11] Patent Number: 5,156,619
[45] Date of Patent: Oct. 20, 1992

[54] FLANGED END-TO-SIDE VASCULAR GRAFT

[76] Inventor: William K. Ehrenfeld, 31 Via Los Altos, Tiberon, Calif. 94920

[21] Appl. No.: 538,325

[22] Filed: Jun. 15, 1990

[51] Int. Cl.⁵ .............................................. A61F 2/06
[52] U.S. Cl. .......................................... 623/1; 623/12
[58] Field of Search ..................................... 623/1, 12

[56] References Cited

U.S. PATENT DOCUMENTS

| | | | |
|---|---|---|---|
| 3,853,462 | 1/1974 | Smith | 8/130.1 |
| 3,945,052 | 3/1976 | Liebig | 3/1 |
| 3,986,828 | 10/1976 | Hoffman, Jr. et al. | 8/115.5 |
| 4,047,252 | 9/1977 | Liebig et al. | 3/1.4 |
| 4,309,776 | 1/1982 | Berguer | 3/1.4 |
| 4,416,028 | 11/1983 | Eriksson | 3/1.4 |
| 4,503,568 | 3/1985 | Madras | 623/1 |
| 4,517,687 | 5/1985 | Liebig et al. | 3/1.4 |
| 4,728,328 | 3/1988 | Hughes et al. | 623/12 |
| 4,816,028 | 3/1989 | Kapadia | 623/1 |

OTHER PUBLICATIONS

The Manual of Vascular Surgery, vol. I, "Anastomotic and Suture Techniques", by Edwin J. Wylie, et al., pp. 14–29.
The Manual of Vascular Surgery, vol. I, "Renovascular Atherosclerosis": by Edwin J. Wylie, et al., pp. 233–257.

Primary Examiner—David Isabella
Assistant Examiner—Debra S. Brittingham
Attorney, Agent, or Firm—Blum Kaplan

[57] ABSTRACT

A flanged end-to-side vascular graft having an integrally formed flange at at least one end with an opening disposed at a non-right angle to the straight portion of the graft. The upper portion of the flange is shaped to follow a smooth continuous curve and the crotch portion is substantially free of reinforcing stitches. The continuous curve and limited stitches provide a continuous uniform smooth suturing surface to facilitate attachment to a larger artery.

11 Claims, 1 Drawing Sheet

FLANGED END-TO-SIDE VASCULAR GRAFT

BACKGROUND OF THE INVENTION

This invention relates to synthetic vascular grafts, and more particularly to synthetic vascular grafts having an integrally formed flange on at least one end to facilitate end-to-side anastomoses.

Vascular grafts of synthetic materials are widely used for the replacements of segments of human blood vessels. Synthetic vascular grafts have taken a wide variety of configurations and are formed of a wide variety of materials. Among the accepted and successful vascular graft implants are those which are formed from a biologically compatible material which retains an open lumen to permit blood to flow through the graft after implantation. The biologically compatible materials include polyester, polytetrafluoroethylene (PTFE), silicone and polyurethanes. The most widely used are polyester fibers and PTFE. The polyester fibers (usually Dacron) may be knitted or woven and may be of a monofilament, multifilament or staple yarn.

There are a wide variety of synthetic vascular grafts presently in use. An important factor in the selection of a particular graft substrate is the porosity of the substrate of which the graft is formed and the strength requirements. Porosity of the graft is significant because it controls the tendency to hemorrhage during and after implantation and influences ingrowth of tissue into the wall of the graft. Synthetic fabric vascular grafts may be of a woven, knit or velour construction. A warp-knit graft is disclosed in U.S. Pat. No. 3,945,052 and a warp knit double-velour construction is disclosed in U.S. Pat. No. 4,047,252. A synthetic woven double-velour substrate is described in U.S. Pat. No. 4,517,687.

These issued United States patents for synthetic vascular grafts are assigned to the assignee of this application. After knitting or weaving the grafts are compacted and then crimped to provide the crimping which facilitates maintaining the open lumen during flexing of the graft. Methods of compacting are shown in U.S. Pat. Nos. 3,853,462 and 3,986,828.

Most operations requiring transection of a vessel involve end-to-end anastomoses. However, there is a large number of end-to-side anastomoses. Simple or bleak transection of a graft to be used for an end-to-side anastomoses may tend to create a short zone of arterial constriction at the apex of the graft unless extreme care is used in the placement of the graft and sutures during implant.

It has been a known and useful technique for anastomosing a tubular fabric graft to the side of the aorta when a small graft is necessary to match the size of the artery to which it is to be connected distally. If for example, an aorta-to-celiac graft requiring a 6-mm graft is appropriate, the graft can be cut from a 12×6 bifurcation preserving a flange from its aortic segment. This flange has allowed for rapid placement of the sutures in the aortic wall without the risk of serious narrowing of the stoma.

An example of this technique is shown in FIG. 1 wherein a bifurcated polyester fiber graft 11 having a main body segment 12 and two legs 13 and 14. Legs 13 and 14 are joined to main body 12 at a crotch 15 which is usually reinforced by a row of stitches 17 to maintain as tight an initial porosity of the graft as possible and maintain its integrity during handling after weaving or knitting. Stitches 17 are necessary to close the space in crotch 16 between legs 13 and 14 which forms during knitting or weaving. Graft 11 is formed of a polyester fiber, either knit or woven, compacted and given a series of circular crimps 16 about main body 12 and legs 13 and 14.

In order to use graft 11 for an end-to-side anastomoses, graft 11 has been cut along a line 18. This provides a flanged graft 21 as shown in FIG. 2 having a straight portion 22 with an integrally formed flange portion 23. An illustration of placement of graft 21 along an artery wall 24 and secured by sutures 26 is shown in FIG. 3.

While this technique has been followed for some time with success, the results are not entirely satisfactory and it is desirable to provide a flanged end-to-side vascular graft of improved construction. The difficulty with graft 21 is that the graft is harvested from bifurcated graft with crotch 16 reinforced with stitches 17. The reinforcement is hard and tends to cause crotch 16 to curve towards back toward straight portion 22 and makes it difficult to suture. Stitches 17 cause breaks or bends in suturing needles which can tend to tear the artery when end-to-side graft 21 is being attached. Efforts at avoiding this difficulty by cutting crotch wider has not been successful and the problems noted above continue to plague the vascular surgeon.

Accordingly, it is desirable to provide an improved synthetic flanged end-to-side vascular graft including an integral flange which avoids the difficulties present in the prior art.

SUMMARY OF THE INVENTION

A flanged end-to-side vascular graft having an integrally formed flange on at least one end with a crotch portion which does not tend to fold towards the straight portion of the graft and which has an improved design for easy attachment to a main artery is provided. The upper portion of the flange is shaped to follow a smooth continuous curve or a portion of the arc of a circle for facilitating suturing. The lower or crotch region of the flange preferably is maintained substantially free of reinforcing stitches to prevent folding of the flange towards the straight portion of the graft. When stitching is used to close any opening formed during manufacture, the stitches should be done by hand and not extend to the periphery of the flange in order to provide a soft continuous suturing surface about the periphery of the flange.

Accordingly, it is an object of the invention to provide an improved flanged vascular graft.

It is another object of the invention to provide an improved flanged vascular graft for end-to-side anastomoses.

It is a further object of the invention to provide an end-to-side flanged vascular graft which is easier to suture by providing a crotch substantially free of reinforcing stitches.

Still another object of the invention is to provide an improved flanged end-to-side vascular graft wherein the upper portion of the flange is shaped in a continuous round curve.

Still other objects and advantages of the invention will in part be obvious and will in part be apparent from the specification.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
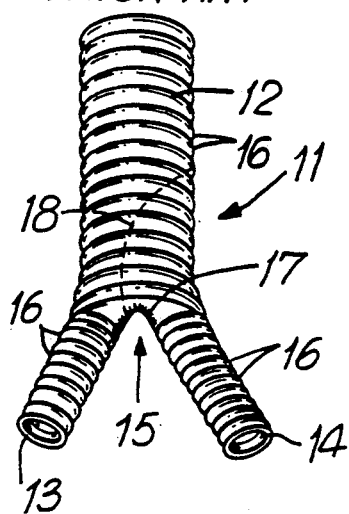
FIG. 1 is a plan view of a conventional bifurcated synthetic fabric vascular graft.
Figure 2:
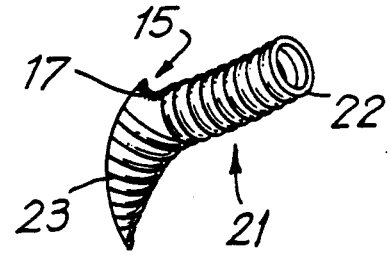
FIG. 2 is a plan view of a flanged end-to-side vascular graft harvested from the bifurcated graft of FIG. 1.
Figure 3:
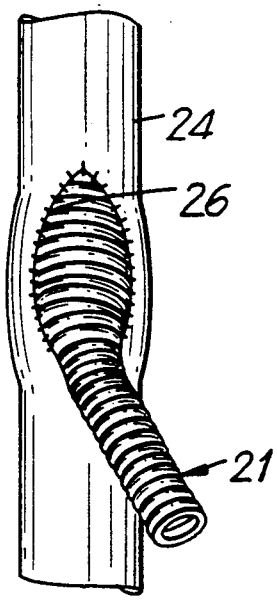
FIG. 3 is a plan view of the flanged end-to-side vascular graft of FIG. 2 anastomosized to the side of an aorta
Figure 4:
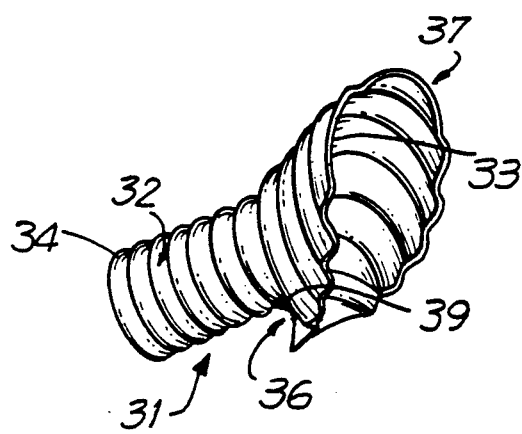
FIG. 4 is a plan view of the flanged end-to-side of vascular graft prepared in accordance with the invention.
Figure 5:
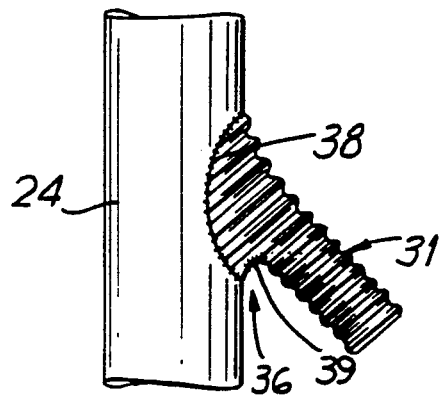
FIG. 5 is an elevational view illustrating the graft of FIG. 4 anastomosized to the side of the aorta.

FIG. 4 illustrates end-to-side vascular graft 31 prepared in accordance with the invention. Graft 31 includes a straight portion 32 with an integrally formed flange portion 33. Graft 31 is formed in the usual manner of fabricating a synthetic fabric vascular graft and after compaction has been given a plurality of crimps 34 along straight portion 32 and continuously extending t flange portion 33. Graft 31 is similar in construction to graft 21 of FIG. 2, however differs in two significant respects. Specifically, graft 31 includes a crotch region 36 which is substantially free of reinforcing stitches. Additionally, the upper region 37 opposite to crotch region 36 is formed in the shape of a continuous curve, and in a preferred embodiment upper region 37 of flange portion 33 follows the arc of a circle. Graft 31 is anastomosized to aorta 24 in the usual manner by sutures 38 as illustrated in the side view in FIG. 5.

The structural differences between end-to-side vascular prosthesis 31 prepared in accordance with the invention and graft 21 as typically cannibalized from bifurcated graft 11 provide significant benefits during implantation. By providing crotch 36 substantially free of stitches 17 present in graft 21 eliminates a difficulty in suturing the crotch portion of flange 23 to the main artery. Stitches 17 which are usually machine stitches, previously led to bending and breaking of suturing needles. This is a significant problem to the patient receiving the vascular prosthesis since a broken or bent needle used during suturing could tear the artery wall. Stitches 17 also lengthen the period of time necessary to suture graft 21 to artery 24 thereby exposing the patient to additional risks.

In order to avoid this, crotch 36 of graft 31 prepared in accordance with the invention is substantially free of stitches and does not include any machine stitching. Any stitches 39 present are necessary to close any opening formed during manufacture and are placed by hand. This insures that stitches 39 are soft and do not extend to the periphery of flange 23 at crotch 36 so as to provide an even continuous suturing surface about the periphery of flange 33. Upper region 37 of flange 33 in prosthesis 31 in accordance with the invention is rounded and formed in the shape of a continuous flowing curve. This is in contrast to the pointed ellipse-type shape of prosthesis 21 previously utilized. The smooth curve of upper region 37 preferably follows the arc of a circle and facilitates the easy suturing along suturing line 38. This allows the vascular surgeon to complete the placement of prosthesis 31 on artery 24 wall in an expedited and efficient manner. This increase in efficiency leads to a more rapid placement of prosthesis 31 thereby further reducing risk to a patient.

The periphery of flange 33 lies at an angle to the axis of straight portion 32. This facilitates placement for an aorta-renal graft, an iliac-splenic graft and an iliac-femoral graft.

While prosthesis 31 has been described in connection with a typical 6 mm strength portion 32, it is to be understood that the configuration of prosthesis 31 is suitable for use in a wide variety of sizes from 4 to 12 mm and typically 5 to 8 mm for end-to-side anastomoses along the aorta wall. In addition to the decrease in time necessary to implant prosthesis 31 due to the improved construction, the construction of graft 31 tends to prevent narrowing of the lumen of straight portion 31 in the region of crotch 36. These structural features all provide an ideal and similar sewing surface about the entire periphery of flange 33 thereby reducing risks to the recipient. While the structural changes in prosthesis 31 compared to graft 21 may be considered minor, the benefits noted are significant.

Prosthesis 31 illustrated in FIG. 4 is made of 100% texturized Dacron yarn construction. The yarn is knitted which provides an inner surface suitable for rapid development of a thin, well anchored neointima, as well as an outer wall that promotes rapid through-the-wall healing for firm incorporation of inner and outer capsules. Typical porosity of such a graft is 1700 $cc/mm/cm^2$ to promote rapid healing. This construction is particularly well suited for end-to-side grafts to be anchored to the artery wall in view of the lower porosity than typical knitted grafts with sufficient strength to withstand the pressures applied when stepping down in graft size.

It will thus be seen that the objects set forth above, among those made apparent from the preceding description, are efficiently attained and, since certain changes may be made in the above product without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An end-to-side flanged woven or knitted tubular vascular graft, comprising:

a substantially cylindrical first straight portion of a first diameter, said first straight portion having a longitudinal axis, and a flange portion integrally formed with the first straight portion, said flange portion defining a second tubular portion of a second diameter larger than the first diameter, said flange portion terminating at a periphery defined by a plane which forms an acute angle with said longitudinal axis; said flange having an upper arcuate region and a lower crotch region, said crotch defined by an angular junction between the first straight portion and said flange, wherein the crotch region along the periphery of said flange is substantially free of stitches so as to provide an even, continuous suturing surface about said periphery of said flange.

2. The prosthesis of claim 1, wherein the upper region of the flange opposite to the crotch region is a smooth continuous curve.

3. The prosthesis of claim 2, wherein the curve is substantially circular.

4. The prosthesis of claim 1, wherein the angle formed by the plane including the periphery of the flange intersects the plane including the axis of the straight portion at an angle between 30° to 60°.

5. The prosthesis of claim 4, wherein the angle is between about 40° to 50°.

6. The prosthesis of claim 2, wherein the angle formed by the plane including the periphery of the flange intersects the plane including the axis of the straight portion at an angle between 30° to 60°.

7. The prosthesis of claim 6, wherein the angle is between about 40 to 50°.

8. The prosthesis of claim 1, wherein the prosthesis is formed of a synthetic fabric.

9. The prosthesis of claim 8, wherein the synthetic fabric is texturized polyester.

10. The prosthesis of claim 8, wherein the fabric is knitted.

11. The prosthesis of claim 8, wherein the fabric is woven.

* * * * *